(12) United States Patent
Coy et al.

(10) Patent No.: US 7,408,024 B2
(45) Date of Patent: Aug. 5, 2008

(54) SOMATOSTATIN ANTAGONISTS

(75) Inventors: David H. Coy, New Orleans, LA (US); William A. Murphy, Slidell, LA (US); Walajapet G. Rajeswaran, Kalamazoo, MI (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 11/894,231

(22) Filed: Aug. 20, 2007

(65) Prior Publication Data

US 2008/0020970 A1    Jan. 24, 2008

Related U.S. Application Data

(63) Continuation of application No. 10/469,836, filed as application No. PCT/US02/06676 on Mar. 5, 2002.

(60) Provisional application No. 60/274,308, filed on Mar. 8, 2001.

(51) Int. Cl.
A61K 38/31 (2006.01)
A61K 38/00 (2006.01)

(52) U.S. Cl. .................. 530/311; 530/345; 530/300; 514/2; 514/806

(58) Field of Classification Search ............... 530/311, 530/345, 300; 514/2, 806
See application file for complete search history.

(56) References Cited

U.S. PATENT DOCUMENTS

| 5,506,339 A | 4/1996 | Coy et al. |
| 5,552,520 A | 9/1996 | Kim et al. |
| 5,569,741 A | 10/1996 | Coy et al. |
| 5,750,499 A | 5/1998 | Hoeger et al. |
| 5,846,934 A | 12/1998 | Bass et al. |
| 6,930,088 B2 | 8/2005 | Hornik et al. |

FOREIGN PATENT DOCUMENTS

| EP | 0 273 696 | 7/1988 |
| EP | 0 278 158 | 8/1988 |
| EP | 0 328 090 A2 | 8/1989 |
| EP | 0 671 413 | 9/1995 |
| GB | 2 206 352 | 1/1989 |
| JP | S63-146850 A | 7/1988 |
| JP | S63-264497 A | 11/1988 |
| JP | 64-26599 | 1/1989 |
| JP | H6-509075 A | 10/1994 |
| JP | 7-258108 | 10/1995 |
| WO | WO 93/03058 | 2/1993 |
| WO | WO 98/08529 | 3/1998 |
| WO | WO 98/10786 | 3/1998 |
| WO | WO 98/24807 A2 | 6/1998 |
| WO | WO 98/24807 | 7/1998 |
| WO | WO 02/070555 | 9/2002 |
| WO | WO 02/072602 | 9/2002 |
| WO | WO 02/081499 | 10/2002 |

OTHER PUBLICATIONS

Wound healing (2007, updated) Research—Angiogenesis and wound healing, http://www.cumc.columbia.edu/dept/cs/cli/wound/angiogenesis.htm, p. 1. I.*
Hocart, et al., 1998. "Potent Antagonists of Somatostatin: Synthesis and Biology," J. Med. Chem. 41:1145-1154.
Hocart, et al., 1999. "Highly Potent Cyclic Disulfide Antagonists of Somatostatin," J. Med. Chem. 42:1863-1871.
Bass, R. T. et al., 1996. "Identification and characterization of novel somatostatin antagonists," Mol. Pharmacology, 50:709-715.
Briard et al., 1997. "Species differences between male rat and ram pituitary somatostatin receptors . . . ", Eur. J. Endocrinol. 137(5): 545-555.

* cited by examiner

*Primary Examiner*—Karen Cochrane Carlson
*Assistant Examiner*—Samuel Wei Liu
(74) *Attorney, Agent, or Firm*—Yankwich & Assoc.; Alan F. Feeney; Pamela C. Ball (57) ABSTRACT

The present invention is directed to a somatostatin antagonist according to formula (I): $A^1$-cyclo {D-Cys-$A^2$-D-Trp-$A^3$-$A^4$-Cys}-$A^5Y^1$, wherein $A^1$ is an optionally substituted aromatic a-amino acid; $A^2$ is an optionally substituted aromatic α-amino acid; $A^3$ is Dab, Dap, Lys or Orn; $A^4$ is β-Hydroxyvaline, Ser, Hser, or Thr; $A^5$ is an optionally substituted D- or L-aromatic amino acid; and $Y^1$ is OH, $NH_2$ or $NHR^{1'}$ where $R^{1'}$ is ($C_{1-6}$)alkyl; wherein each said optionally substituted aromatic amino acid is optionally substituted with one or more substituents each independently selected from the group consisting of halogen, $NO_2$, OH, CN, ($C_{1-6}$) alkyl, ($C_{2-6}$) alkenyl, ($C_{2-6}$) alkynyl, ($C_{1-6}$)alkoxy, Bzl, O-Bzl, and $NR^9R^{10'}$ wherein $R^9$ ad $R^{10}$ each is independently H, O, or ($C_{1-6}$) alkyl; and wherein the amine nitrogen of each of amide peptide bond and the amino group of $A^1$ of formula (I) is optionally substituted with a methyl group, provided that there is at least one said methyl group; or a pharmaceutically acceptable salt thereof, and is directed to uses thereof.

9 Claims, 1 Drawing Sheet

Figure 1: In vitro Inhibition of hsstr-5 Mediated Intracellular Ca2+ Mobilization

SOMATOSTATIN ANTAGONISTS

This application is a continuation application of pending U.S. Ser. No. 10/469,836, filed Feb. 24, 2004, which is a United States national filing under 35 U.S.C. §371 of international (PCT) application No. PCT/GB02/06676, filed Mar. 5, 2002, designating the United States, and claiming priority to U.S. Provisional Application No. 60/274,308, filed Mar. 8, 2001.

BACKGROUND OF THE INVENTION

Somatostatin (SRIF), a tetradecapeptide discovered by Brazeau et al., has been shown to have potent inhibitory effects on various secretory processes in tissues such as pituitary, pancreas and gastrointestinal tract. SRIF also acts as a neuromodulator in the central nervous system. These biological effects of SRIF, all inhibitory in nature, are elicited through a series of G protein coupled receptors, of which five different subtypes have been characterized ($sstr_1$-$sstr_5$). These five subtypes have similar affinities for the endogenous SRIF ligands but have differing distribution in various tissues. Somatostatin binds to the five distinct receptor (SSTR) subtypes with relatively high and equal affinity for each subtype. Binding to the different types of somatostatin subtypes have been associated with the treatment of various conditions and/or diseases. ("$sstr_2$") (Raynor, et al., Molecular Pharmacol. 43:838 (1993); Lloyd, et al., Am. J. Physiol. 268:G102 (1995)) while the inhibition of insulin has been attributed to the somatostatin type-5 receptor ("$sstr_5$") (Coy, et al. 197: 366-371(1993)). Activation of types 2 and 5 have been associated with growth hormone suppression and more particularly Growth hormone GH secreting adenomas (Acromegaly) and TSH secreting adenomas. Activation of type 2 but not type 5 has been associated with treating prolactin secreting adenomas. Other indications associated with activation of the somatostatin receptor subtypes are inhibition of insulin and/or glucagon for treating diabetes mellitus, angiopathy, proliferative retinopathy, dawn phenomenon and nephropathy; inhibition of gastric acid secretion and more particularly peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis, treatment of inflammatory disorders such as arthritis; retinopathy; chronic allograft rejection; angioplasty; preventing graft vessel and gastrointestinal bleeding. It is preferred to have an analog which is selective for the specific somatostatin receptor subtype or subtypes responsible for the desired biological response, thus, reducing interaction with other receptor subtypes which could lead to undesirable side effects.

The development of potent, smaller SRIF agonists led to the discovery of differing affinities of the various truncated ligands for the different subtypes. It appears that $Trp^8$-$Lys^9$ sequence often is present in ligands that are recognized by the receptor. The $Trp^8$-$Lys^9$ sequence forms part of a β-bend which is usually stabilized via substitution of D- for L-Trp, cyclization of the backbone, a disulfide bridge, or all constraints. One unintended consequence of such structural simplification, carried out before the discovery of multiple receptor subtypes, was the loss of broad spectrum binding affinity. This is typified by the high type 2 but low type 1, 3, 4, and 5 affinities of peptides in the OCTREOTIDE® series. Thus, the many basic biological studies with this type of analog failed to detect effects mediated by all but one of the somatostatin receptor types. Since then, much work has gone into the re-introduction of broader spectrum binding into small, biologically stable peptides on the one hand and the development of peptides and peptidomimetics with discrete specificity for a particular receptor.

We have discovered that peptide backbone constraint can be introduced by N-alkylation of individual amino acids. This modification largely restricts the affected residue and the amino acid preceding it to an extended conformation. Thus, additionally blocks potential intramolecular hydrogen bonding sites and also proteolytic enzyme cleavage sites thus potentially enhancing the pharmacokinetic properties of a peptide. Only a few N-methyl amino acids are commercially available and their synthesis is tedious. However, in another aspect of the present invention, we have discovered a procedure to N-methylate truncated somatostatin analogs at every amino acid residue using the solid-phase procedure, adopted from the recent publication reported by Miller and Scanlan.

SUMMARY OF THE INVENTION

In one aspect, the present invention is directed to a peptide of the formula (I), $A^1$-cyclo{D-Cys-$A^2$-D-Trp-$A^3$-$A^4$-Cys}-$A^5$-$Y^1$,     (I)

wherein:
$A^1$ is an optionally substituted aromatic α-amino acid;
$A^2$ is an optionally substituted aromatic α-amino acid;
$A^3$ is Dab, Dap, Lys or Orn;
$A^4$ is β-Hydroxyvaline, Ser, Hser, or Thr;
$A^5$ is an optionally substituted D- or L-aromatic α-amino acid; and
$Y^1$ is OH, $NH_2$ or $NHR^1$, where $R^1$ is $(C_{1-6})$alkyl;

wherein each said optionally substituted aromatic α-amino acid is optionally substituted with one or more substituents each independently selected from the group consisting of halogen, $NO_2$, OH, CN, $(C_{1-6})$alkyl, $(C_{2-6})$alkenyl, $(C_{2-6})$alkynyl, $(C_{1-6})$alkoxy, Bzl, O-Bzl, and $NR^9R^{10}$, where $R^9$ and $R^{10}$ each is independently H, O, or $(C_{1-6})$ alkyl; and wherein the amine nitrogen of each of amide peptide bond and the amino group of $A^1$ of formula (I) is optionally substituted with a methyl group, provided that there is at least one said methyl group; or a pharmaceutically acceptable salt thereof.

In one embodiment the invention features peptides of formula (I) wherein:
$A^1$ is Cpa, 1-Nal, 2-Nal, 2-Pal, 3-Pal, 4-Pal, Phe, Tfm, Tyr or Tyr(I);
$A^2$ is 2-Pal, 3-Pal, 4-Pat, Phe, Tyr or Tyr(I); and
$A^5$ is Dip, 1-Nal, 2-Nal, 2-Pal, 3-Pal, 4-Pal, Phe or D-Trp;

or a pharmaceutically acceptable salt thereof.

In another embodiment the invention features a peptide of the immediately foregoing group of peptides wherein $A^1$ is Cpa.

In a further embodiment the invention features a peptide of the immediately foregoing group of peptides wherein $A^3$ is NMeLys.

In a still further embodiment the invention features a peptide of formula (I) wherein said peptide is:

NmeCpa-cyclo(DCys-3-Pal-DTrp-Lys-Thr-Cys)-2-Nal-$NH_2$;

Cpa-cyclo(NMeDCys-3-Pal-DTrp-Lys-Thr-Cys)-2-Nal-NHMe;

Cpa-cyclo(DCys-NMe3-Pal-DTrp-Lys-Thr-Cys)-2-Nal-$NH_2$;

Cpa-cyclo(DCys-3-Pal-NMeDTrp-Lys-Thr-Cys)-2-Nal-NH$_2$;

Cpa-cyclo(DCys-3-Pal-DTrp-NMeLys-Thr-Cys)-2-Nal-NH$_2$;

Cpa-cyclo(DCys-3-Pal-DTrp-Lys-NMeThr-Cys)-2-Nal-NH$_2$;

Cpa-cyclo(DCys-3-Pal-DTrp-Lys-Thr-NMeCys)-2-Nal-NH$_2$;

Cpa-cyclo(DCys-3-Pal-DTrp-Lys-Thr-Cys)-Nme2-Nal-NH$_2$;

Cpa-cyclo(NMeDCys-3-Pal-DTrp-Lys-Thr-Cys)-Dip-NHMe;

Cpa-cyclo(DCys-3-Pal-NMeDTrp-NMeLys-Thr-Cys)-2-Nal-NH$_2$;

Cpa-cyclo(DCys-Tyr-DTrp-NMeLys-Thr-Cys)-2-Nal-NH$_2$;

Tfm-cyclo(DCys-3-Pal-DTrp-NMeLys-Thr-Cys)-2-Nal-NH$_2$;

Cpa-cyclo(DCys-3-Pal-DTrp-NMeLys-Thr-Cys)-DTrp-NH$_2$;

Nal-cyclo(DCys-3-Pal-DTrp-NMeLys-Thr-Cys)-DTrp-NH$_2$; or

3-Pal-cyclo(DCys-3-Pal-DTrp-NMeLys-Thr-Cys)-DTrp-NH$_2$;

or a pharmaceutically acceptable salt thereof.

In yet a further embodiment the invention features a peptide of formula (I) wherein said peptide is:

NmeCpa-cyclo(DCys-3-Pal-DTrp-Lys-Thr-Cys)-2-Nal-NH$_2$;

Cpa-cyclo(DCys-3-Pal-DTrp-NMeLys-Thr-Cys)-2-Nal-NH$_2$;

Cpa-cyclo(DCys-3-Pal-NMeDTrp-NMeLys-Thr-Cys)-2-Nal-NH$_2$;

Cpa-cyclo(DCys-Tyr-DTrp-NMeLys-Thr-Cys)-2-Nal-NH$_2$;

Cpa-cyclo(DCys-3-Pal-DTrp-NMeLys-Thr-Cys)-DTrp-NH$_2$;

Nal-cyclo(DCys-Pal-DTrp-NMeLys-Thr-Cys)-DTrp-NH$_2$; or

3-Pal-cyclo(DCys-3-Pal-DTrp-NMeLys-Thr-Cys)-DTrp-NH$_2$;

or a pharmaceutically acceptable salt thereof.

In still yet a further embodiment the invention features a peptide of formula (I) wherein said peptide is:

NmeCpa-cyclo(DCys-3-Pal-DTrp-Lys-Thr-Cys)-2-Nal-NH$_2$;

Cpa-cyclo(DCys-3-Pal-DTrp-NMeLys-Thr-Cys)-2-Nal-NH$_2$;

Cpa-cyclo(DCys-3-Pal-NMeDTrp-NMeLys-Thr-Cys)-2-Nal-NH$_2$;

Cpa-cyclo(DCys-Tyr-DTrp-NMeLys-Thr-Cys)-2-Nal-NH$_2$; or

Cpa-cyclo(DCys-3-Pal-DTrp-NMeLys-Thr-Cys)-DTrp-NH$_2$;

or a pharmaceutically acceptable salt t hereof.

In still yet a further embodiment the invention features a peptide of the immediately foregoing group of peptides wherein said peptide is:

Cpa-cyclo(DCys-3-Pal-DTrp-NMeLys-Thr-Cys)-2-Nal-NH$_2$; or

Cpa-cyclo(DCys-Tyr-DTrp-NMeLys-Thr-Cys)-2-Nal-NH$_2$;

or a pharmaceutically acceptable salt thereof.

In another aspect of the present invention is featured a method of binding one or more somatostatin subtype re cep-tors -1, -2, -3, -4 and -5, which comprises the step of contacting a compound of claim 1 or a pharmaceutically acceptable salt thereof with one or more of said somatostatin subtype receptors.

In one embodiment of the immediately foregoing aspect the present invention features a method of binding one or more somatostatin subtype receptor s -1, -2, -3, -4 and -5 in a human subject or other animal subject, which comprises the step of administering an effective amount of a compound of claim 1 or a pharmaceutically acceptable salt thereof to a subject in need thereof.

In another embodiment aspect of the present invention is featured a method of eliciting a somatostatin antagonist effect from a cell, wherein said cell comprises one or more somatostatin receptors, said method comprising contacting said cell with an effective amount of a compound of claim 1 or a pharmaceutically acceptable salt thereof.

In another embodiment, the present invention provides a method for eliciting a somatostatin antagonist effect in a human subject or other animal subject, which comprises the step of administering an effective amount of a compound of claim 1 or a pharmaceutically acceptable salt thereof to a subject in need thereof.

In a further embodiment of the present invention is featured a method of promoting the release of growth hormone in a human or animal subject, which comprises administering to said subject an effective amount of a compound according to claim 1 or a pharmaceutically acceptable salt thereof.

In another embodiment of the present invention is featured a method of promoting the release of insulin in a human or animal subject in need thereof, which comprises administering to said subject an effective amount of a compound according to claim 1 or a pharmaceutically acceptable salt thereof.

In another embodiment of the present invention is featured a method of enhancing wound healing in a human or animal subject in need thereof, which comprises administering to said subject an effective amount of a compound according to claim 1 or a pharmaceutically acceptable salt thereof.

In yet another embodiment of the present invention is featured a method of promoting angiogenesis in a human or animal subject in need thereof, which comprises administering to said subject an effective amount of a compound according to claim 1 or a pharmaceutically acceptable salt thereof.

In another embodiment of the present invention is featured a method of treating a disease or condition in a human or other animal subject in need thereof, which comprises the step of administering an effective amount of a compound of claim 1 or a pharmaceutically acceptable salt thereof to said subject, wherein said disease or condition is selected from the group consisting of short stature, cachexia, wasting, type 2 diabetes, poor circulation, and the like.

In another aspect of the present invention is featured a method of imaging cells having somatostatin receptors which comprises contacting said cells with an effective amount of a compound according to claim 1, or a pharmaceutically acceptable salt thereof, which comprises Tyr(I).

DETAILED DESCRIPTION

One skilled in the art can, based on the description herein, utilize the present invention to its fullest extent. The following specific embodiments are, therefore, to be construed as merely illustrations of the invention and are not meant to be construed as limiting the full scope of the invention.

As is well known to those skilled in the art, the known and potential uses of somatostatin are varied and multitudinous. Somatostatin and analogs thereof are known to be useful in the treatment of the diseases and/or conditions listed hereinbelow. The varied uses of somatostatin may be summarized as follows: Cushings Syndrome (see Clark, R. V. et al, Clin. Res. 38, p. 943A, 1990); gonadotropinoma (see Ambrosi B., et al., Acta Endocr. (Copenh.) 122, 569-576, 1990); hyperparathyroidism (see Miller, D., et al., Canad. Med. Ass. J., Vol. 145, pp. 227-228, 1991); Paget's disease (see, Palmieri, G. M. A., et al., J. of Bone and Mineral Research, 7, (Suppl. 1), p. S240 (Abs. 591), 1992); VIPoma (see Koberstein, B., et al., Z. Gastroenterology, 28, 295-301, 1990 and Christensen, C., Acta Chir. Scand. 155, 541-543, 1989); nesidioblastosis and hyperinsulinism (see Laron, Z., Israel J. Med. Sci., 26, No. 1, 1-2, 1990, Wilson, D.C., Irish J. Med. Sci., 158, No. 1, 31-32, 1989 and Micic, D., et al., Digestion, 16, Suppl. 1.70. Abs. 193, 1990); gastrinoma (see Bauer, F. E., et al., Europ. J. Pharmacol., 183, 55 1990); Zollinger-Ellison Syndrome (see Mozell, E., et al., Surg. Gynec. Obstet., 170, 476-484, 1990); hypersecretory diarrhea related to AIDS and other conditions (due to AIDS, see Cello, J. P., et al., Gastroenterology, 98, No. 5, Part 2, Suppl., A163 1990; due to elevated gastrin-releasing peptide, see Alhindawi, R., et al., Can. J. Surg., 33, 139-142, 1990; secondary to intestinal graft vs. host disease, see Bianco J. A., et al., Transplantation, 49, 1194-1195, 1990; diarrhea associated with chemotherapy, see Petrelli, N., et al., Proc. Amer. Soc. Clin. Oncol., Vol. 10, P 138, Abstr. No. 417 1991); irritable bowel syndrome (see O'Donnell, L. J. D., et al., Aliment. Pharmacol. Therap., Vol. 4., 177-181, 1990); pancreatitis (see Tulassay, Z., et al., Gastroenterology, 98, No. 5, Part 2, Suppl., A238, 1990); Crohn's Disease (see Fedorak, R. N., et al., Can. J. Gastroenterology, 3, No. 2, 53-57, 1989); systemic sclerosis (see Soudah, H., et al., Gastroenterology, 98, No. 5, Part 2, Suppl., A129, 1990); thyroid cancer (see Modigliani, E., et al., Ann., Endocr. (Paris), 50, 483-488, 1989); psoriasis (see Camisa, C., et al., Cleveland Clinic J. Med., 57-No. 1, 71-76, 1990); hypotension (see Hoeldtke, R. D., et al., Arch. Phys. Med. Rehabil., 69, 895-898, 1988 and Kooner, J. S., et al., Brit. J. Clin. Pharmacol., 28, 735P-736P, 1989); panic attacks (see Abelson, J. L., et al., Clin. Psychopharmacol., 10, 128-132, 1990); scierodoma (see Soudah, H., et al., Clin. Res., Vol. 39, p. 303A, 1991); small bowel obstruction (see Nott, D. M., et al., Brit. J. Surg., Vol. 77, p. A691, 1990); gastroesophageal reflux (see Branch, M. S., et al., Gastroenterology, Vol. 100, No. 5, Part 2 Suppl., p. A425, 1991); duodenogastric reflux (see Hasler, W., et al., Gastroenterology, Vol. 100, No. 5, Part 2, Suppl., p. A448, 1991); Graves' Disease (see Chang, T. C., et al., Brit. Med. J., 304, p. 158, 1992); polycystic ovary disease (see Prelevic, G. M., et al., Metabolism Clinical and Experimental, 41, Suppl. 2, pp 76-79, 1992); upper gastrointestinal bleeding (see Jenkins, S. A., et al., Gut., 33, pp. 404-407, 1992 and Arrigoni, A., et al., American Journal of Gastroenterology, 87, p. 1311, (abs. 275), 1992); pancreatic pseudocysts and ascites (see Hartley, J. E., et al., J. Roy. Soc. Med., 85, pp. 107-108, 1992); leukemia (see Santini, et al., 78, (Suppl. 1), p. 429A (Abs. 1708), 1991); meningioma (see Koper, J. W., et al., J. Clin. Endocr. Metab., 74, pp. 543-547, 1992); and cancer cachexia (see Bartlett, D. L., et al., Surg. Forum., 42, pp. 14-16, 1991). The contents of the foregoing references are incorporated herein by reference.

The peptides of the invention are useful as antagonists to the activity or activities of somatostatin. For example, the peptides of the invention can be used to promote the release of growth hormone or insulin in a subject (e.g., a mammal such as a human patient). Thus, the peptides are useful in the treatment of physiological conditions in which the promotion of the release of growth hormone or insulin is of benefit. The peptides of the invention can also be used in enhancing wound healing or promoting angiogenesis. Further, peptides of the invention having a Tyr(I) residue can be used to image cells containing somatostatin receptors. Such peptides of the invention can be used either in vivo to detect cells having somatostatin receptors (e.g., cancer cells) or in vitro as a radioligand in a somatostatin receptor binding assay. The peptide of the invention can also be used as vectors to target cells with radioactive isotopes.

Also contemplated within the scope of this invention is a peptide covered by the above generic formula for both use in treating diseases or disorders associated with the need to promote the release of growth hormone or insulin, and use in detecting somatostatin receptors, e.g., radioimaging.

A compound of formula (I) or a pharmaceutically-acceptable salt thereof can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 25 μg/kg/day to 100 mg/kg/day of body weight daily are administered as a single dose or divided into multiple doses to humans and other animals, e.g., mammals, to obtain the desired therapeutic effect.

A preferred general dosage range is 250 μg/kg/day to 5.0 mg/kg/day of body weight daily which can be administered as a single dose or divided into multiple doses.

Further, a compound of formula (I) can be administered in a sustained release composition such as those described in the following patents. Among those formulations, 14-day or 28-day slow release formulations will be preferred. U.S. Pat. No. 5,672,659 teaches sustained release compositions comprising a peptide and a polyester. U.S. Pat. No. 5,595,760 teaches sustained release compositions comprising a peptide in a gelable form. U.S. Pat. No. 5,821,221 teaches polymeric sustained release compositions comprising a peptide and chitosan. U.S. Pat. No. 5,916,883 teaches sustained release compositions comprising a peptide and cyclodextrin. International Patent Application No. PCT/US99/01180, (publication no. WO 99/38536, Aug. 5, 1999), teaches absorbable sustained release compositions of a peptide. The contents of the foregoing patents and applications are incorporated herein by reference.

The use of immediate or of sustained release compositions depends on the type of indications targeted. If the indication consists of an acute or over-acute disorder, a treatment with an immediate form will be preferred over the same with a prolonged release composition. On the contrary, for preventive or long-term treatments, a prolonged release composition will generally be preferred.

Abbreviations

The nomenclature for the somatostatin receptor subtypes is in accordance with the recommendations of IUPHAR, in which $sstr_4$ refers to the receptor originally cloned by Bruno et al., and $sstr_5$ refers to the receptor cloned by O'Carroll et al.

Abbreviations of the common amino acids are in accordance with the recommendations of IUPAC-IUB. Further, as used herein the definitions for certain abbreviations are as follows:

Abu=α-aminobutyric acid;
Aib=α-aminoisobutyric acid;
β-Ala=β-alanine;
Amp=4-amino-phenylalanine;
Ava=5-aminovaleric acid;
Cha=cyclohexylalanine;
Cpa=3-(4-chlorophenyl)alanine;
Dab=2,4-diaminobutyric acid;
Dap=2,3-diaminopropionic acid;
Dip=3,3'-diphenylalanine;
Gaba=γ-aminobutyric acid;
HSer=homoserine;
1-Nal=3-(1-naphthyl)alanine;
2-Nal=3-(2-naphthyl)alanine;
Nle=norleucine;
Nva=norvaline;
2-Pal=3-(2-pyridyl)alanine;
3-Pal=3-(3-pyridyl)alanine;
4-Pal=3-(4-pyridyl)alanine;
Tfm=Trifluoromethyl; and
TfmA=4-trifluoromethylphenyl-alanine.
Tyr(I)=An iodinated tyrosine residue (e.g., 3-1-Tyr, 5-I-Tyr, 3,5-I-Tyr) wherein the iodine may be a radioactive isotope, e.g., $I_{125}$, $I_{127}$, or $I_{131}$.

The following abbreviations of certain reagents also appear herein:

DBU=1,8-diazabicyclo[5.4.0]undec-7-ene;
DCM=dichloromethane;
DIC=diisopropylcarbodiimide;
DIEA=diisopropyethylamine;
DMF=dimethylfornamide;
MTBD=1,3,4,6,7,8-Hexahydro-1-methyl-2H-pyrimido[1,2-a]pyrimidine;
o-NBS=2-nitrobenzenesulfonyl;
TBTU=O-Benzotriazol-1-yl-N,N,N',N'-tetramethyluronium tetrafluoroborate;

and

TFA=trifluoroacetic acid.

With the exception of the N-terminal amino acid, all abbreviations (e.g., Cpa for $A^1$) of amino acids in this disclosure stand for the structure of —NH—CH(R)—CO—, wherein R is the side chain of an amino acid (e.g., $CH_3$ for Ala). For the N-terminal amino acid, the abbreviation stands for the structure of $(R^1R^2)$—N—CH(R)—CO—, wherein R is a side chain of an amino acid and each of $R^1$ and $R^2$ is independently H or as otherwise defined herein.

An aliphatic amino acid is an α-amino acid having one or two side chains which, independently, are hydrocarbons, e.g., a straight or branched chain of 1-6 carbons. Examples of aliphatic amino acids include Ala, Aib, Val, Leu, Tle, Ile, Nle, Nva, or Abu.

What is meant by "aromatic α-amino acid" is an amino acid residue of the formula where $Z_1$ is a moiety containing an aromatic ring and $Z_2$ is hydrogen or a moiety containing an aromatic ring. Examples of such aromatic ring-containing moieties include, but are not limited to, a benzene or pyridine ring and the following structures with or without one or more substituent X on the aromatic ring (where X is, independently for each occurrence, halogen, $NO_2$, $CH_3$, $OCH_3$, $CF_3$, or OH):

Other examples of an aromatic α-amino acid of the invention are substituted His, such as MeHis, His (τ-Me), or His (π-Me).

As used herein, "alkyl" is intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl and the like. When the term $C_0$-alkyl is included in a definition it is intended to denote a single covalent bond.

The term "lower alkyl" is intended to include both branched and straight-chain alkyl groups having 1-6 carbon atoms.

As used herein, "aryl", is intended to include any stable monocyclic, bicyclic, or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl, and the like.

The term "heterocyclyl", as used herein, represents a stable 5- to 7-membered monocyclic or stable 8- to 11-membered bicyclic or stable 11-15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, quinoxalinyl, tetrahydrofuryl, tetrahydroisoquinolinyl, tetrahydroisoquinolinyl, tetrahydro-quinolinyl, thiamorpholinyl, thiamorpholinyl sulfoxide, thiazolyl, thiazolinyl, thienofuryl, thienothienyl, thienyl, and the like.

The term "substituted" is meant to include the recited chemical group (e.g., lower alkyl, aryl, cycloalkyl, etc.) substituted with one or more of the recited substituents (e.g., halo, hydroxy, lower alkyl, etc.). The substituent may be attached to any atom in the chemical group.

The abbreviation "NMe" stands for "N-methyl-". As used herein NMe indicates that the amide nitrogen of the associated amino acid is methylated. Thus, "NmeCpa" indicates —N(CH$_3$)—CH(R)—CO— where R is 4-chlorophenyl, "Nme2-Nal" indicates —N(CH$_3$)—CH(R)—CO— where R is 2-naphthyl, and so forth.

The term alkoxy is intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term halogen or halo is intended to include the halogen atoms fluorine, chlorine, bromine and iodine.

When the amino acid residue is optically active, it is the L-form that is intended unless the D-form is expressly designated.

Materials

4-Methylbenzhydrylamine hydrochloride resin (0.25 or 0.5 mequiv g$^{-1}$) was obtained from Advanced ChemTech Inc., Louisville, Ky. N$^\alpha$ tert-Butyloxycarbonyl (Boc) protected amino acids were purchased from Bachem Inc., Torrance, Calif., Advanced ChemTech Inc., and Synthetech Inc., Albany, Oreg. The reactive side-chains of the amino acids were masked with one of the following groups: Cys, 4-methylbenzyloxycarbonyl; Lys, 2-chlorobenzyloxycarbonyl; Thr, O-benzyl; Tyr, O-2,6-dichlorobenzyl. All reagents and solvents were ACS grade or better and used without further purification.

Peptide Synthesis

The peptide synthesis may be summarized by the following reaction

Scheme:

-continued

The compounds of formula (I) can be and were synthesized on 4-methylbenzhydrylamine functionalized, 1% cross-linked polystyrene resin (0.25 or 0.5 mequiv g$^{-1}$), in 0.25 mmol scale on an Advanced ChemTech (model 200) synthesizer, using the following protocol: deblocking, 40% TFA (2 min, 20 min); DCM wash cycle (three washes); neutralization, 10% DIEA (1 min, 5 min); DMF wash cycle; DCM wash cycle (two washes); double coupling; first with 1,3-diisopropyl carbodiimide esters (3 equiv.), 30 min in DCM; DCM wash (three washes); second coupling with preformed TBTU esters (3 equiv.), 90 min in DMF, with a catalytic amount of DIEA; DMF wash (one wash); DCM wash (three washes). Coupling reactions are monitored qualitatively.

N$^\alpha$-Protection

After deblocking the amino group at the desired methylation site, the resin was suspended in DCM (20 mL). To this suspension, collidine (3 equiv.) and o-nitrobenzenesulfonyl chloride (3 equiv.) are added and the mixture was shaken using Advanced ChemTech (model 200) synthesizer for 2 h. Then the resin was subjected to DCM wash (2 washes) and DMF wash (3 washes). Protection is monitored qualitatively by the ninhydrin test.

N$^\alpha$-Methylation

The o-nitrobenzenesulfonamide protected resin was suspended in DMF (20 mL), to which MTBD (3 equiv.) and methyl 4-nitrobenzenesulfonate or dimethyl sulfate (for Cys$^{11}$) was added. The mixture was shaken using Advanced ChemTech (model 200) synthesizer for 0.5 h and the resin was subjected to DMF wash (4 washes).

N$^\alpha$—Me Deprotection

Once the desired residue was methylated, the resin was again suspended in DMF (20 mL). DBU (3 equiv.) and 2-mercaptoethanol (3 equiv.) were added to the suspension and the mixture was agitated for 0.5 h in Advanced ChemTech (model 200) synthesizer. The resin was then thoroughly washed with DMF (5 washes).

The foregoing methylation procedure worked well for all residues except for D-Cys$^6$, which resulted in dimethylated derivatives, (see, e.g., compounds 2 and 10.) However replacement of D-Cys$^6$ with Cys$^6$ gave monomethylated peptides.

Peptide Cleavage

The peptides were cleaved from the resin support with simultaneous side-chain deprotection by acidolysis using anhydrous hydrogen fluoride containing the scavenger anisole (~30% v/v) for 45 min at 0° C. The peptides were cyclized in 90% acetic acid (~600 mL) with a slight excess of I$_2$ (15 min). Excess I$_2$ was then removed by the addition of ascorbic acid.

Purification

The crude peptides were purified by preparative RP-HPLC on C-18 bonded silica gel using axial compression columns (Dynamax-300 Å, 5 or 8 μm, 21.4×250 mm). A linear gradient elution system at a flow rate of 20 mL min$^{-1}$ was employed: A; 0.1% TFA, B; 0.1% TFA in 80% MeCN, 20% B to 50% B at 1% min$^{-1}$. The separations were monitored by analytical RP-HPLC at 215 nm. The fractions containing the product were pooled, concentrated in vacuo and subjected to lyophilization. Each peptide was obtained as a fluffy white powder of constant weight by lyophilization from aqueous acetic acid. The purity of the final peptides was assessed at 215 nm by analytical RP-HPLC. Analytical RP-HPLCs were recorded using a Vydac C-18 support (4.6×250 mm, 5 μm, 300 Å pore size, Liquid Separations Group). The- linear gradient system was used at a flow rate of 1.5 mL min$^{-1}$: HPLC-1, A, 0.1% TFA; B, 0.1% TFA in 80% MeCN; 20% B to 50% B at 1% min$^{-1}$; HPLC-2, C, 5% MeCN in TEAP (0.1 M, pH 3); D, 20% C in MeCN, 10% D to 70% D at 1% min$^{-1}$. Column eluent was monitored at 215 nm. The retention time and purity of each peptide was assessed by the Rainin Dynamax HPLC Method Manager. Each peptide was found to have a purity of >98%. The HPLC retention time results are given in Table 1.

TABLE 1

N-Methyl Analogs and Analytical Data

| | | Mass Spectrum (M – H$^+$) | | HPLC$^c$ | |
| --- | --- | --- | --- | --- | --- |
| Peptide No. | N-Me Sequence | Calcd.$^a$ | Obsd.$^b$ | $(t_{R-1})^d$ | $(t_{R-2})^e$ |
| 1 | NmeCpa-cyclo(DCys-3-Pal-DTrp-Lys-Thr-Cys)-2-Nal-NH$_2$ | 1178.7 | 1179.2 | 18.3 | 19.3 |
| 2 | Cpa-cyclo(NmeDCys-3-Pal-DTrp-Lys-Thr- | 1192.7 | 1193.4 | 19.6 | 19.3 |

TABLE 1-continued

N-Methyl Analogs and Analytical Data

| Peptide No. | N-Me Sequence | Mass Spectrum (M − H⁺) Calcd.[a] | Obsd.[b] | HPLC[c] $(t_{R-1})$[d] | $(t_{R-2})$[e] |
|---|---|---|---|---|---|
|  | Cys)-2-Nal-NHMe |  |  |  |  |
| 3 | Cpa-cyclo(DCys-Nme3-Pal-DTrp-Lys-Thr-Cys)-2-Nal-NH₂ | 1178.7 | 1178.9 | 20.3 | 22.5 |
| 4 | Cpa-cyclo(DCys-3-Pal-NMeDTrp-Lys-Thr-Cys)-2-Nal-NH₂ | 1178.7 | 1179.2 | 17.9 | 17.2 |
| 5 | Cpa-cyclo(DCys-3-Pal-DTrp-NMeLys-Thr-Cys)-2-Nal-NH₂ | 1178.7 | 1178.9 | 19.2 | 18.7 |
| 6 | Cpa-cyclo(DCys-3-Pal-DTrp-Lys-NMeThr-Cys)-2-Nal-NH₂ | 1178.7 | 1179.3 | 17.4 | 15.1 |
| 7 | Cpa-cyclo(DCys-3-Pal-DTrp-Lys-Thr-NmeCys)-2-Nal-NH₂ | 1178.7 | 1179.0 | 18.5 | 16.7 |
| 8 | Cpa-cyclo(DCys-3-Pal-DTrp-Lys-Thr-Cys)-(Nme)-2-Nal-NH₂ | 1178.7 | 1179.0 | 20.3 | 19.0 |
| 9 | Cpa-cyclo(DCys-3-Pal-DTrp-Lys-Thr-Cys)-Nal-NH₂ | 1164.8 | 1164.7 | 17.2 | 17.2 |
| 10 | Cpa-cyclo(NMeDCys-3-Pal-DTrp-Lys-Thr-Cys)-Dip-NHMe | 1218.9 | 1218.9 | 21.9 | 20.8 |
| 11 | Cpa-cyclo(DCys-3-Pal-NMeDTrp-NMeLys-Thr-Cys)-2-Nal-NH₂ | 1192.7 | 1192.3 | 19.9 | 19.7 |
| 12 | Cpa-cyclo(DCys-Tyr-DTrp-NMeLys-Thr-Cys)-2-Nal-NH₂ | 1193.8 | 1193.6 | 24.9 | 23.1 |
| 13 | Tfm-cyclo(DCys-3-Pal-DTrp-NMeLys-Thr-Cys)-2-Nal-NH₂ | 1212.2 | 1212.2 | 21.4 | 20.7 |
| 14 | Cpa-cyclo(DCys-3-Pal-DTrp-NMeLys-Thr-Cys)-DTrp-NH₂ | 1167.8 | 1168.0 | 16.6 | 14.9 |
| 15 | Nal-cyclo(DCys-3-Pal-DTrp-NMeLys-Thr-Cys)-DTrp-NH₂ | 1183.2 | 1183.5 | 18.0 | 16.4 |
| 16 | 3-Pal-cyclo(DCys-3-Pal-DTrp-NMeLys-Thr-Cys)-DTrp-NH₂ | 1135.0 | 1134.8 | 11.5 | 9.8 |

[a]Theoretical molecular weight (M − H⁺, Da).
[b]Observed molecular weight (M − H⁺, Da).
[c]Reversed-phase HPLC (C-18, 5 μm, 4.6 × 250 mm, λ = 215 nm) retention times (min). Each compound was found to have a purity of >98% by HPLC.
[d]HPLC Elution System: A; 0.1% TFA, B; 0.1% TFA in 80% MeCN, 20% B to 50% B at 1% min$^{-1}$ and 1.5 mL min$^{-1}$.
[e]HPLC-2 elution system: C, 5% MeCN in TEAP (0.1M, pH 3); D, 20% C in MeCN, 10% D to 50% D at 1% min$^{-1}$ and 1.5 mL min$^{-1}$.

Amino Acid Analysis

The peptides were hydrolyzed in vacuo (110° C.; 20 h) in 4 M methanesulfonic acid containing 0.2% 3-(2-aminoethyl) indole (Pierce). Amino acid analyses were performed on the hydrolyzates following derivatization with o-phthalidaldehyde reagent (Sigma Chemical Co.) using an automatic HPLC system (Rainin Instrument Co.) fitted with a 100×4.6 mm, 3 μm C18 axial compression column with integral guard column (Microsorb AAAnalysis™, Type O; Rainin Instrument Co.) The derivatized primary amino acids were eluted using a binary gradient of buffer A; 0.10 M sodium acetate containing 4.5% v/v methanol and 0.5% v/v tetrahydrofuran at pH 7.2 and buffer B; methanol. The gradient sequence; 0% A at 0 min; 35% A at 16.5 min; 90% A at 30 min and 90% A at 33 min is used with a flow rate of 1.0 mL min$^{-1}$ at ambient temperature. Eluent is monitored at 340 nm and integrated by the Dynamax HPLC Method Manager (Rainin). Standard retention times were as follows: Asp, 6.6 min; Arg, 19.9 min; Trp, 25.4 min and Lys, 29.5 min. Each peptide of Table I produced the expected analytical results for the primary amino acids. Cysteine is not quantified.

Mass Spectrometry

The peptides were analyzed by matrix-assisted laser desorption/ionization time-of-flight mass spectrometry using a LaserMat 2000 mass spectrometer (Thermal Bioanalysis, San Jose, Calif.) using α-cyano-4-hydroxycinnamic acid as the matrix with Substance P (1348.7 Da) as an internal standard. In each case, the spectra consisted of a major M–H⁺ ion peak for the internal standard, the expected analyte M–H⁺ peak, and a few peaks associated with the matrix (<500 Da). The results are given in Table 1.

Antagonism of SRIF Inhibition of GH Release

Anterior pituitaries from adult male rats were collected and dispersed by a previously described trypsin/DNase method. (Murphy, W. A.; Taylor, J.; Moreau, J.-P. and Coy, D. H., Peptide Res. 1989, 2, 128-132.) The dispersed cells were diluted with sterile-filtered Dulbecco's modified Eagle medium (MEM, Gibco Laboratories, Grand Island, N.Y.), which was supplemented with 2.5% fetal calf serum (Gibco), 3% horse serum (Gibco), 10% fresh rat serum (stored on ice for no longer than 1 h) from the pituitary donors, 1% MEM nonessential amino acids (Gibco), gentamycin (10 ng mL$^{-1}$; Sigma) and nystatin (10,000 U mL$^{-1}$; Gibco). The cells were randomly plated at a density of approximately 200,000 cells/ well (Costar cluster 24; Rochester Scientific Co., Rochester, N.Y.). The plated cells were maintained in the above Dulbecco's medium in a humidified atmosphere of 95% air/5% CO₂ at 37° C. for 4-6 days. In preparation for a hormone challenge, the cells were washed with medium 199 (Gibco, 3×1 mL). Each dose of a compound of this invention (6 doses/plate) was tested in triplicate wells in the presence of 1 nM SRIF in a total volume of 1 nL medium 199 containing 1% BSA (fraction V; Sigma Chemical Co.). All wells contained growth hormone releasing hormone GHRH(1-29)NH₂ (1 nM). A GHRH(1-29)NH$_2$ (1 nM) stimulated control group and an SRIF (1 nM) with GHRH(1-29)NH$_2$ (1 nM) inhibited control group were included on each cell culture plate. After 3 h incubation in an air/carbon dioxide atmosphere (95/5%, 3 h at 37° C.), the medium was removed and stored at −20° C. until assayed for hormone content. Growth hormone in media was measured by a standard double antibody RIA using components generously supplied by Dr. A. F. Parlow at the National Hormone and Pituitary Program (NHHP) Torrance, Calif.

Antagonist IC$_{50}$'s versus SRIF (1 nM) were calculated using Sigmaplot (Jandel Scientific, San Rafael, Calif.). Values are expressed as the mean IC$_{50}$ (nM)±SEM and are given in Table 2.

Receptor Expression and Transfection

Transfections were performed by the calcium phosphate method. CHO-K1 cells are maintained in α-minimum essential medium (α-MEM; Gibco) supplemented with 10% fetal calf serum and transfected with each of the expression plasmids using calcium phosphate precipitation. Clones that had inherited the expression plasmid were selected in α-MEM supplemented with 500 µg mL$^{-1}$ of geneticin (G418; Gibco). Independent CHO-K1 clones were picked by glass-ring cloning and expanded in culture in the selective media. Membranes were prepared from the isolated clones and hsstr expression was initially assessed for binding with [$^{125}$I]Tyr$^{11}$-SRIF and [$^{125}$I]MK-678 (for sstr$_2$).

TABLE 2

Binding Affinities (K$_i$) for Cloned Human sst$_{1-5}$ Receptors and Antagonist Data

| Peptide No. | N$^α$-Methylation site | K$_i$$^a$ ± SEM (nM) | | | | | Antagonist IC$_{50}$ ± SEM (nM)$^b$ |
|---|---|---|---|---|---|---|---|
| | | hsst$_1$ | hsst$_2$ | hsst$_3$ | hsst$_4$ | hsst$_5$ | |
| SRIF-14 | N/A$^c$ | 2.0 ± 0.35 | 0.25 ± 0.03 | 1.2 ± 0.2 | 2.0 ± 0.3 | 1.4 ± 0.3 | N/A$^c$ |
| SRIF-28 | N/A$^c$ | 1.9 ± 0.4 | 0.31 ± 0.06 | 1.3 ± 0.3 | 5.4 ± 2.5 | 0.4 ± 0.1 | N/A$^c$ |
| 1 | Cpa$^5$ | 1000 | 36 ± 7.6 | 330 ± 126 | 1000 | 40.1 ± 18.8 | 7.8 ± 2.7 |
| 2$^d$ | D-Cys$^6$ | 1000 | 89.0 ± 8.0 | 576 ± 47 | 1000 | 106 ± 36 | nd$^e$ |
| 3 | 3-Pal$^7$ | 1000 | 189.0 ± 35 | 450 ± 132 | 1000 | 1000 | nd$^e$ |
| 4 | D-Trp$^8$ | 1000 | 51.8 ± 2.6 | 390 ± 114 | 1000 | 93 ± 17.7 | nd$^e$ |
| 5 | Lys$^9$ | 1000 | 17.1 ± 5.5 | 66.0 ± 5.8 | 1000 | 5.98 ± 0.91 | 0.73 ± 0.33 |
| 6 | Thr$^{10}$ | 395 ± 202 | 1000 | 315 ± 12.5 | 1000 | 88.5 ± 45.7 | nd$^e$ |
| 7 | Cys$^{11}$ | 1000 | 810 | 68.7 ± 4.7 | 575 | 161 ± 52 | nd$^e$ |
| 8 | 2-Nal$^{12}$ | 1000 | 197 ± 55 | 1000 | 1000 | 1000 | nd$^e$ |
| 9 | N/A$^c$ | 1395 | 12.1 ± 1.9 | 38.2 ± 2.4 | 1000 | 140 ± 4.6 | 2.6 ± 0.7 |
| 10$^d$ | D-Cys$^6$ | 1000 | 117 ± 24.6 | 584 ± 305 | 1000 | 766 ± 110 | nd$^e$ |
| 11 | DTrp$^8$ & Lys$^9$ | 1000 | 9.33 ± 0.62 | 140 ± 10.4 | 1000 | 112 ± 19 | 2.5 ± 0.20 |
| 12 | Lys$^9$ | 1000 | 5.51 ± 1.85 | 115.1 ± 16.9 | 1000 | 70.7 ± 25.8 | 0.53 ± 0.17 |
| 13 | Lys$^9$ | 1000 | 11.3 | 40.2 | 1246 | 45.5 | nd$^e$ |
| 14 | Lys$^9$ | 1000 | 5.45 ± 0.3 | 91.4 ± 11.9 | 1000 | 101 ± 14.1 | 11.6 ± 4.2 |
| 15 | Lys$^9$ | 1000 | 27.3 ± 1.45 | 148 ± 13.2 | 1000 | 176 ± 65.1 | 96 ± 13.8 |
| 16 | Lys$^9$ | 1000 | 24.7 ± 1.61 | 537 ± 44.8 | 1000 | 313 ± 4.1 | 287 ± 138 |

$^a$Expressed as the mean ± SEM, single values indicate the results of one binding experiment.
$^b$Rat in vitro antagonist IC$_{50}$ (nM) versus SRIF (1.0 nM), expressed as the mean ± SEM.
$^c$Not applicable.
$^d$Peptides 2 and 10 are different peptides.
$^e$Not determined.

Functional Expression of the Cloned Human Somatostatin Receptors

The genomic clones containing the human somatostatin receptors (hsstr$_{1-5}$) (Yamada, Y., et al. al., Proc. Natl. Acad. Sci. USA. 1992, 89, 251-255; Yasuda, K., et al., J. Biol. Chem. 1992, 267, 20422-20428; Yamada, Y., et al., Mol. Pharmacol. 1992, 42, 2136-2142; Rohrer, L., et al., Proc. Natl. Acad. Sci. USA. 1993, 90, 4196-4200.), were kindly provided by Dr. Graeme I. Bell (University of Chicago). The hsstr$_1$, hsstr$_2$, hsstr$_3$, hsstr$_4$ and hsstr$_5$ cDNAs were isolated as a 1.5-kb PstI-XmnI fragment, 1.7-kb BamHI-HindIII fragment, 2.0-kb NcoI-HindIII fragment, 1.4-kb NheI-NdeI fragment, and a 1.2-kb HindIII-XbaI fragment, respectively, each containing the entire coding region of the full-length receptors. These fragments were independently subcloned into the corresponding restriction endonuclease sites in the mammalian expression vector pCMV5, downstream from the human cytomegalovirus (CMV) promoter, to produce the expression plasmids pCMV5/hsstr$_1$, pCMV5/hsstr$_2$, pCMV5/hsstr$_3$, pCMV5/hsstr$_4$ and pCMV5/hsstr$_5$. For transfection into CHO-K1 cells, a plasmid, pRSV-neo (American Type Culture Collection, Rockville, Md.), carrying the neomycin mammalian cell selectable marker was added.

Radioligand Binding Assays

Cell membranes of the 5 receptor types were obtained from homogenates (Polytron setting 6, 15 sec) of the corresponding CHO-K1 cells, in ice-cold Tris-HCl (50 mM) and centrifuged (39000 g, 10 min×2), with an intermediate resuspension in fresh buffer. The final pellets are resuspended in Tris-HCl (10 mM) for assay. Aliquots of the membranes are incubated (30 min at 37° C.) with 0.05 nM [$^{125}$I]Tyr$^{11}$-SRIF (types 1,3,4,5) or [$^{125}$I]MK-678 (type 2) in 50 mM HEPES (pH 7.4) containing BSA (10 mg mL$^{-1}$); MgCl$_2$ (5 mM), Trasylol (200 kIU mL$^{-1}$), bacitracin (0.02 mg mL$^{-1}$), and phenylmethanesulfonyl fluoride (0.02 mg mL$^{-1}$). The final assay volume is 0.3 mL and incubations are terminated by rapid filtration through GF/C filters pre-soaked in 0.3% poly (ethylenimine) using a Brandel rapid filtration module. Each tube and filter is then washed with aliquots of cold buffer (3×5 mL).

Specific binding is. defined as the total radioligand bound minus that bound in the presence of 1.0 µM SRIF. The following total radioligand binding and non-specific binding (nsb) values are typically obtained with these assay systems: hsstr$_1$, 7000 cpm total versus 3500 cpm nsb; hsstr$_2$, 9000 cpm total versus 1000 cpm nsb; hsstr$_3$, 8000 cpm total versus 1000 cpm nsb; hsstr$_4$, 6000 cpm total versus 3500 cpm nsb; and hsstr$_5$, 7500 cpm total versus 3500 cpm nsb. The binding affinities are expressed as K$_i$ values±SEM (nM) for each of the five receptor subtypes and are given in Table 2.

Type 5 Mediated Intracellular Ca$^{2+}$ Mobilization

CHO-K1 cells, expressing the human sst5 receptor, were harvested by incubating in a 0.3% EDTA/phosphate buffered saline solution (25° C.), and washed twice by centrifugation. The washed cells were resuspended in Hank's—buffered saline solution (HBSS) for loading of the fluorescent Ca$^{2+}$ indicator Fura-2AM. Cell suspensions of approximately 10$^6$ cells/ml were incubated with 2 µM Fura-2AM for 30 min at about 25° C. Unloaded Fura-2AM was removed by centrifugation twice in HBBS, and the final suspensions were transferred to a spectrofluorometer (Hitachi F-2000) equipped with a magnetic stirring mechanism and a temperature-regulated cuvette holder. After equilibration to 37° C., the somatostatin peptides were added for measurement of intracellular Ca$^{2+}$ mobilization. The excitation and emission wavelengths were 340 and 510 nm, respectively.

Figure 1:
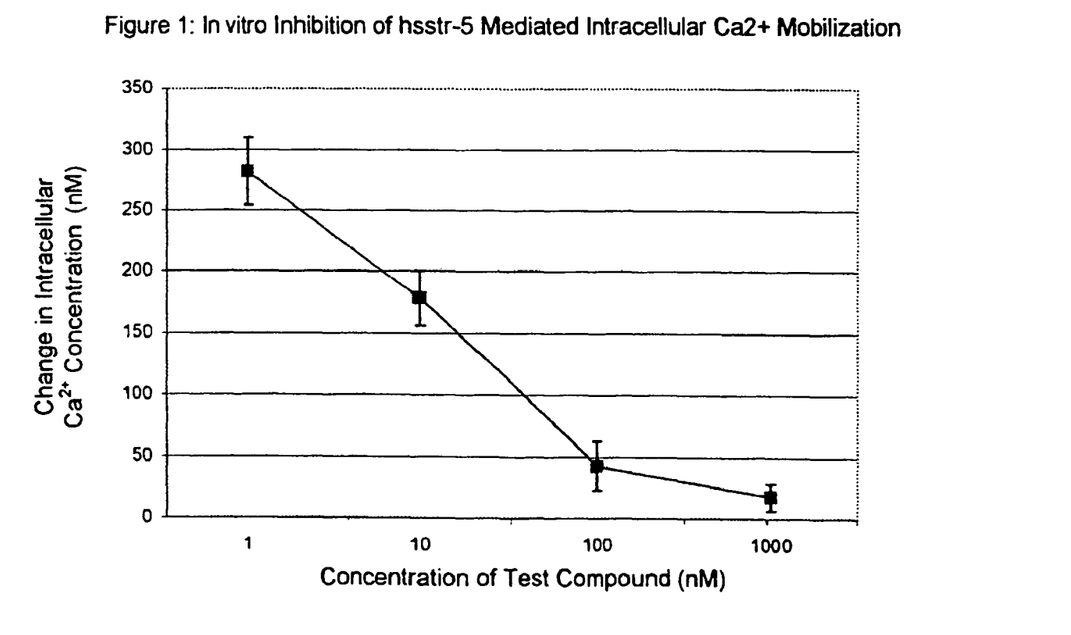
FIG. 1 is a graph showing the in vitro inhibition of hsstr-5 mediated intracellular Ca2+ mobilization.

Exemplary data appears in FIG. 1 which depicts results from the immediately foregoing assay using Analog 5 as the Test Compound.

Molecular Modeling

Molecular modeling was performed on a Silicon Graphics Indigo$^2$ High Impact 10000 computer, using SYBYL molecular modeling software, version 6.6, (Tripos Associates Inc., St. Louis Mo., USA), with the Kollman all atom force field. (Weiner, S. J., et al., J. Comp. Chem. 1986, 7, 230-252.) The PDB files for the three solution NMR structures of the initial compound Sandostatin/Octreotide; D-Phe$^5$-c[Cys$^6$-Phe$^7$-D-Trp$^8$-Lys$^9$-Thr$^{10}$-Cys$^{11}$]-Thr$^{12}$-ol (1SOC and 2SOC) were obtained from the PDB database. These structures were imported into SYBYL 6.6 and mutated to form the N-methylated compounds based on analog 9. The Koliman partial atomic charges were loaded from the monomer dictionary. The structures were optimized by annealing the mutated residue and then by full energy minimization using the conjugate gradient algorithm to a final root mean square (rms) gradient of ≦0.01 Kcal molÅ$^{-1}$. A distance-dependent dielectric function (McCammon, J. A., et al., Biochem. 1979, 18, 927-942) was employed together with the default settings for all the other minimization options. The results are detailed in Table 3.

TABLE 3

Kollman all atom energy change on sequential methylation of each residue of Cpa-cyclo(DCys-3-Pal-DTrp-Lys-Thr-Cys)-2-Nal-NH$_2$ (analogue 9) in each of the three solution conformations expressed as Kcal mol$^{-1}$.

| Analogue No | Methylation Site | I | II | III |
|---|---|---|---|---|
| 1 | NMeCpa$^5$ | −2 | 0.4 | −1 |
| 2 | NMeDCys$^6$, NHMe | 17 | 12 | 31 |
| 3 | NMe3-Pal$^7$ | 7 | 17 | 6 |
| 4 | NMeDTrp$^8$ | 5 | 6 | 5 |
| 5 | NMeLys$^9$ | 6 | 6 | 5 |
| 6 | NMeThr$^{10}$ | 16 | 10 | 12 |
| 7 | NMeCys$^{11}$ | 12 | 14 | 23 |
| 8 | Nme-2-Nal$^{12}$ | 4 | 19 | 7 |

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A somatostatin antagonist compound of the structure NMeCpa-c(D-Cys-3-Pal-D-Trp-Lys-Thr-Cys)-2-Nal-NH$_2$ or a pharmaceutically acceptable salt thereof.

2. A method of binding one or more somatostatin subtype receptors -1, -2, -3, -4 and -5, which comprises the step of contacting the compound of claim 1 or a pharmaceutically acceptable salt thereof with one or more of said somatostatin subtype receptors thereby said binding occurs.

3. A method of eliciting an antagonist effect from an isolated cell, wherein said cell comprises one or more somatostatin receptors, said method comprising contacting said cell with an effective amount of the compound of claim 1 or a pharmaceutically acceptable salt thereby said antagonist effect occurs.

4. A method of eliciting a somatostatin antagonist effect in a human or animal subject, which comprises the step of administering to said subject an effective amount the compound of claim 1 or a pharmaceutically acceptable salt thereof to said subject in need thereof thereby said antagonist effect occurs.

5. A method of promoting the release of growth hormone in a human or animal subject in need thereof, which comprises administering to said subject an effective amount of the compound of claim 1 or a pharmaceutically acceptable salt thereof thereby said promoting the release of growth hormone occurs.

6. A method of promoting the release of insulin in a human or animal subject in need thereof, which comprises administering to said subject an effective amount of the compound of claim 1 or a pharmaceutically acceptable salt thereof thereby said promoting the release of growth hormone occurs.

7. A method of enhancing wound healing in a human or animal subject in need thereof, which comprises administering to said subject an effective amount of the compound of claim 1 or a pharmaceutically acceptable salt thereof thereby said wound healing is enhanced.

8. A method of promoting angiogenesis in a human or animal subject in need thereof, which comprises administering to said subject an effective amount of the compound of claim 1 or a pharmaceutically acceptable salt thereof thereby said promoting angiogenesis occurs.

9. A method of treating a disease or condition in a human or other animal subject in need thereof, which comprises the step of administering an effective amount of a compound of claim 1 or a pharmaceutically acceptable salt thereof to said subject, wherein said disease or condition is selected from the group consisting of short stature, cachexia, wasting, type 2 diabetes, and poor ciculation thereby said disease is treated.

* * * * *